(12) United States Patent
Katou et al.

(10) Patent No.: US 8,179,523 B2
(45) Date of Patent: *May 15, 2012

(54) PHOTOMASK MOUNTING/HOUSING DEVICE AND RESIST INSPECTION METHOD AND RESIST INSPECTION APPARATUS USING SAME

(75) Inventors: Yoshikazu Katou, Tokyo (JP); Takahiro Igeta, Toyko (JP); Hideyuki Moribe, Tokyo (JP); Ryuji Hasegawa, Tokyo (JP)

(73) Assignee: NEC Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/195,593

(22) Filed: Aug. 1, 2011

(65) Prior Publication Data
US 2011/0279816 A1 Nov. 17, 2011

Related U.S. Application Data

(62) Division of application No. 12/341,208, filed on Dec. 22, 2008, now Pat. No. 8,009,285.

(30) Foreign Application Priority Data
Dec. 21, 2007 (JP) .................................. 2007-330488

(51) Int. Cl.
 G01N 21/00 (2006.01)

(52) U.S. Cl. .................. 356/237.1; 356/237.5; 430/5
(58) Field of Classification Search .... 356/237.1–237.5; 430/5, 311, 319; 428/14
See application file for complete search history.

(56) References Cited

U.S. PATENT DOCUMENTS

| 4,697,701 | A | * | 10/1987 | Ying | 206/316.1 |
| 5,168,993 | A | * | 12/1992 | Yen | 206/316.1 |
| 5,820,950 | A | * | 10/1998 | Wang | 428/14 |
| 7,300,526 | B2 | * | 11/2007 | Hedges et al. | 134/33 |
| 7,316,869 | B2 | * | 1/2008 | Eschbach et al. | 430/5 |
| 8,009,285 | B2 | * | 8/2011 | Katou et al. | 356/237.1 |
| 2003/0095245 | A1 | * | 5/2003 | Mishiro et al. | 355/75 |
| 2003/0207182 | A1 | * | 11/2003 | Shirasaki | 430/5 |
| 2004/0012776 | A1 | * | 1/2004 | Bae | 356/237.4 |

* cited by examiner

Primary Examiner — Hoa Pham

(57) ABSTRACT

A resist inspection apparatus is provided which has a configuration in which a reticle is separated from a pellicle. A reticle cassette is made up of two pieces of plate members. A hollowed portion with a shape allowing the reticle to be inserted into the plate member. Another hollowed portion having a shape being slightly larger than that of the resist of the reticle is formed on the plate member. In the circumference of the hollowed portion is placed a pellicle frame on which a protective film is formed in a stretched manner. In the concave portion is housed in the reticle with a resist on the reticle directed toward the hollowed portion. The reticle is put in sealed space.

15 Claims, 5 Drawing Sheets

PHOTOMASK MOUNTING/HOUSING DEVICE AND RESIST INSPECTION METHOD AND RESIST INSPECTION APPARATUS USING SAME

REFERENCE TO RELATED APPLICATION

The present patent application is a divisional application of U.S. patent application Ser. No. 12/341,208, filed Dec. 22, 2008, and which has since issued as U.S. Pat. No. 8,009,285, on Aug. 30, 2011. U.S. Pat. No. 8,009,285 itself claims priority to the Japanese Patent Application No. 2007-330488, filed on Dec. 21, 2007.

BACKGROUND OF THE INVENTION

1. Field of the Invention

The present invention relates to a photomask mounting/housing device and a resist inspection method and resist inspection apparatus using the same and more particularly to the photomask mounting/housing device configured so that a photomask can be easily separated from a translucent protective member and the resist inspection method using the photomask mounting/housing device and the resist inspection apparatus having the photomask mounting/housing device.

2. Description of the Related Art

Conventionally, a photomask (reticle) is used to manufacture semiconductor integrated circuits. Before the photomask is used for manufacturing semiconductor integrated circuits, an inspection is performed to check whether a resist formed on a substrate of a photomask has an expected and predetermined pattern. Various types of technologies have been developed for the inspection of resists. Examples of these technologies are described below.

One example of the related resist inspection apparatus is shown in FIG. 4. As shown in FIG. 4, in the related resist inspection apparatus, light 31 for resist inspection is applied from one side of a reticle 2 and a pattern image is formed based on reflected light fed through an optical element such as a lens 30 and a desired inspection is performed using the obtained pattern image itself or by comparison between the obtained pattern image and a pattern image designed in advance. This example is disclosed in Patent Reference 1 (Japanese Patent Application Laid-open No. Hei06-020934).

Also, in another example of a related resist inspection apparatus whose rough configurations are the same as those shown in FIG. 4, the resist is inspected while air purging is performed on optical elements in the same way as shown in FIG. 4. This example is disclosed, for example, in Patent Reference 2 (Japanese Patent Application Laid-open No. 2006-245400).

Also, in still another example of a related resist inspection apparatus, as shown in FIG. 3, as a photomask to be used in the resist inspection apparatus, a pellicle 3 is coupled to a reticle 2. This example is disclosed in Patent Reference 3 (Japanese Patent Application Laid-open No. 2003-315983).

Furthermore, in still another example of a related resist inspection apparatus, a pellicle frame attached to a pattern surface of a photomask is divided, by pin-coupling, into two portions, an upper frame and a lower frame. This example is disclosed in Patent Reference 4 (Japanese Patent Application Laid-open No. Hei05-216214).

However, the above related technologies have the following problems. That is, in the case of the related resist apparatus disclosed in the Patent Reference 1, when the light 31 for inspection is applied to the resist 7 on the reticle 2, gas 20 is released from the resist 7, which causes the gas 20 to remain, as an adherent 21, on a surface of an optical element such as the lens 30 (see FIG. 6). There is a technological problem that, if the residual adherent 21 occurs at every tine of the inspection, the performance of the optical element of the lens 30 is degraded and finally the inspection becomes impossible. A countermeasure against the degradation of the lens performance is to wipe the adherent 21 off the lens 30, however, it is impossible to fully restore the performance of the lens 30 only by the wiping method and, therefore, unless the lens 30 is replaced, the continuation of the inspection is made impossible. Even in the case where the inspection is to be continued by replacing the lens 30, the lens 30 is expensive and its delivery time is long, thus causing costs to mount and much time to be taken for the repairing process.

The residual adherent 21 caused by the gas presents further problems. That is, if the inspection is performed on another reticle 2b in a state where the adherent 21 is being left, as shown in FIG. 7, the residual adherent 21 causes a difference between a pattern image to be obtained from the inspection and a pattern image designed in advance and, as a result, the difference in pattern is extracted, as a defect, together with an actual defect that may occur in the resist 7b by the image comparing device in the resist inspection apparatus.

If the above information only is used for the comparison, it is made impossible to differentiate between the defect caused by the residual adherent 21 and the actual defect of the resist 7b. In order to achieve the exact differentiation, the further processes of inspection and/or checking are required which include the method by the re-inspection with the reticle 2b rotated horizontally by 90, 180, or 270 degrees, etching of the reticle 2b, detailed checking of the lens 30, or the like.

Out of the above differentiation methods, the re-inspection method by the rotation of the reticle 2b presents a further problem, that is, during the re-inspection process, the adherent 21 is accumulated more, which possibly makes it more difficult to differentiate between the defect caused by the residual adherent 21 and the actual defect of the resist 7b. Also, in the case of the differentiation method by etching the reticle 2b for checking, if an actual defect is found in the resist 7b, the use of the reticle 2b becomes impossible. Furthermore, the method by detailed checking of the lens 30 is practically impossible due to its difficulty and time required for the checking process.

Various countermeasures against the degradation of performance of optical elements such as the lens 30 are available, however, a peculiar technological problem still arises in each of the countermeasures. Therefore, the technological problem related to the degradation of performance of optical elements such as the lens 30 caused by gas remains unsolved. The technological problem related to the degradation of performance of optical elements is partially solved by the technology disclosed in the Patent Reference 2.

However, there is the following technological problem in the above technology using the air purge. In the technology disclosed in the Patent Reference 2, the air purging is performed on the optical element to avoid the direct contact between the gas 20 and lens 30. However, unless the purging air is rectified smoothly to purge the lens 30, the fluctuation of inspection light 31 occurs, as a result, making it difficult to obtain the uniformity of the light 31 which causes unevenness in image to show up and makes it impossible to perform the inspection itself. Furthermore, due to the attachment of the air purging component, difficulties exist in the maintenance of the apparatus.

The technological problem arises in the method disclosed in the Patent Reference 3. That is, if the resist 7 on a photomask is to be inspected by using the method, when the resist 7 is re-formed or etched after the inspection, it is necessary to take out the pellicle 3 or the pellicle 3 together with the pellicle frame 8 from the reticle 2 and, therefore, during the process of the removal, the reticle 2 may be contaminated or damaged.

The Patent Reference 4 discloses the configuration in which a photomask is housed between the two pellicle frames being pin-coupled to each other, thus requiring an upper frame and a lower frame. However, no configuration is suggested in which a photomask is housed in a pellicle frame to which a pellicle is attached in an stretched manner.

SUMMARY OF THE INVENTION

In view of the above, it is an object of the present invention to provide a photomask mounting/housing device in which easy separation between a photomask and a translucent protective member is made possible and a resist inspection method using the photomask mounting/housing device and a resist inspection apparatus having the photomask mounting/housing device.

According to a first aspect of the present invention, there is provided a photomask mounting/housing device for receiving and housing a photomask, including frame bodies each having a concave portion with a shape allowing the photomask to be received and housed and hollowed portions each formed in the concave portion with a shape allowing at least a resist formed region of the photomask to be inserted, and a translucent protective member disposed outside the hollowed portions of the frame bodies and forming sealed space so as to be opposite to and be apart from a resist.

According to a second aspect of the present invention, there is provided a resist inspection method for applying light to a photomask and inspecting a resist of the photomask by receiving reflected light from the photomask, including a step of housing the resist of the photomask into a concave portion of a photomask mounting/housing device having frame bodies each having a concave portion with a shape allowing the photomask to be received and housed and hollowed portions each formed in the concave portion with a shape allowing at least a resist formed region of the photomask to be inserted and a translucent protective member disposed outside the hollowed portions of the frame bodies and forming sealed space so as to be opposite to and be apart from a resist, with the resist of the photomask directed toward the translucent protective member side and a step of applying light from the translucent protective member side to perform inspection of the resist.

According to a third aspect of the present invention, there is provided a resist inspection apparatus for applying light from an optical system to a photomask placed in a photomask placing portion and receiving reflected light from the photomask to perform inspection of a resist of the photomask, including a photomask mounting/housing device to be placed in the photomask placing portion which has frame bodies each having a concave portion with a shape allowing the photomask to be received and housed and hollowed portions each formed in the concave portion with a shape allowing at least a resist formed region of the photomask to be inserted and a translucent protective member disposed outside the hollowed portions of the frame bodies and forming sealed space so as to be opposite to and be apart from a resist and which houses, in its concave portion, resists of the photomask, via the hollowed portion, arranged so as to be directed toward the optical system.

With the above configurations, it is made possible to obtain the device/method that can provide great advantages by separating the photomask from the photomask mounting/housing device and also that serves to achieve effects of preventing the release of gas out of the photomask to maintain the performance of the optical system and of avoiding the replacement of the optical system. Also, by configuring as above, easy replacement of the photomask mounting/housing device and translucent protective film is made possible. Also, by configuring as above, during an inspection of the photomask, no contamination and/or damage of the photomask occurs and inspection processes can be reduced and inspection time can be shortened. Also, easy etching processes after being inspected and easy recoating with resists can be made possible. Also, even when the resist inspection is performed on a plurality of reticles, the optical elements are not affected by gas released from the resist. All that is needed to exclude an influence by the gas is to form the sealed space between the photomask mounting/housing device and translucent protective film and no other device/method of various types are required.

BRIEF DESCRIPTION OF THE DRAWINGS

The above and other objects, advantages, and features of the present invention will be more apparent from the following description taken in conjunction with the accompanying drawings in which.

DETAILED DESCRIPTION OF THE PREFERRED EXEMPLARY EMBODIMENTS

Best modes of carrying out the present invention will be described in further detail using various exemplary embodiments with reference to the accompanying drawings. According to the present invention, a concave portion is formed in a photomask mounting/housing device into which a photomask is housed. Moreover, the photomask mounting/housing device in which the photomask is housed in its concave portion is used by a resist inspection apparatus.

First Exemplary Embodiment

Figure 1:
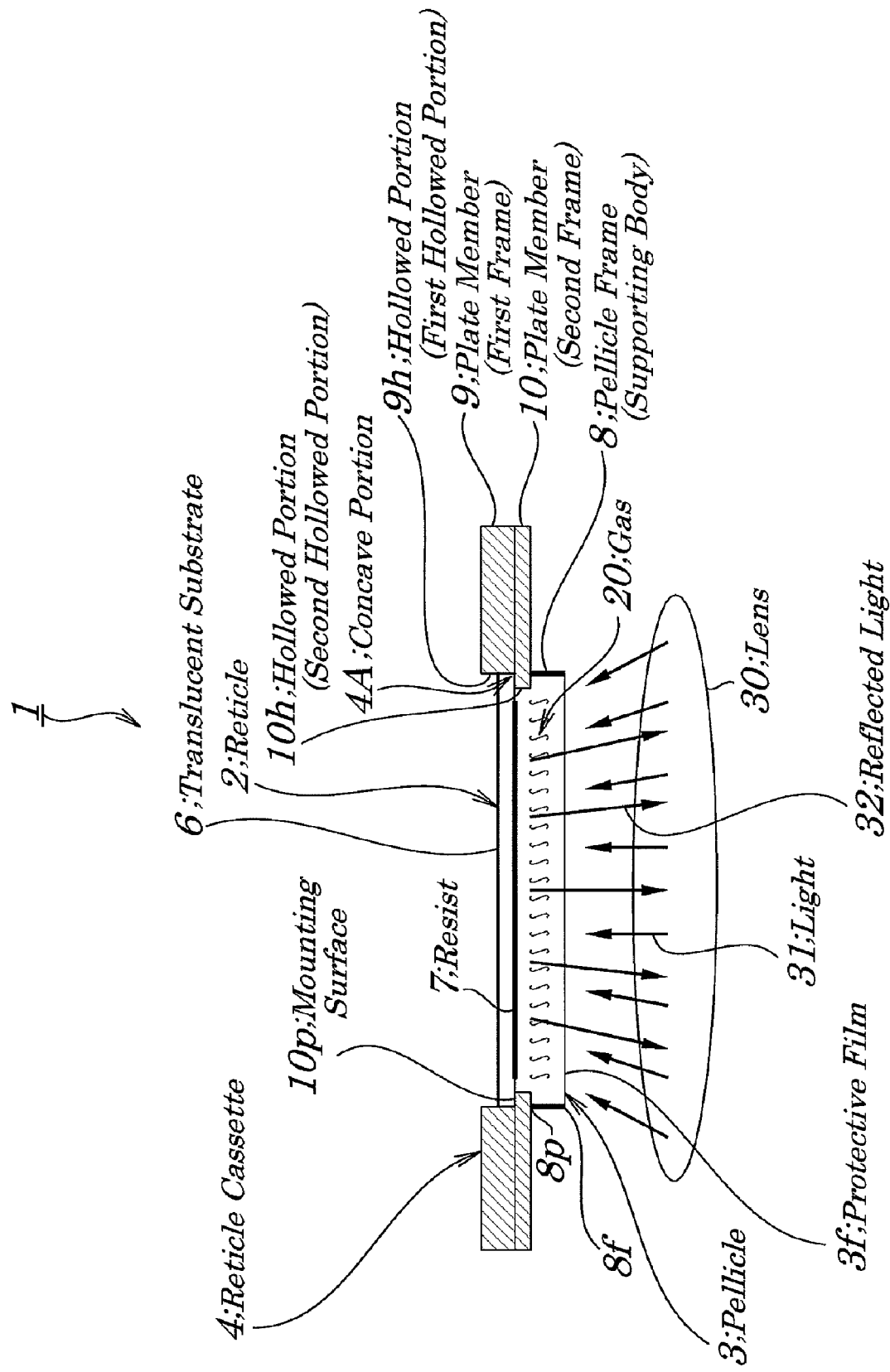
FIG. 1 is a diagram showing a reticle mounting/housing device according to a first exemplary embodiment of the present invention.

FIG. 1 is a diagram showing a reticle mounting/housing device of the first exemplary embodiment of the present invention. In the reticle mounting/housing device 1 of the first exemplary embodiment, no mechanical and rigid coupling exists between a reticle 2 and pellicle 3 connected to a reticle cassette 4. The reticle 2 is housed in a concave portion formed in the reticle cassette 4 and the reticle cassette 4 is placed in a resist inspection apparatus to be used for the inspection of a resist coated on the reticle 2.

The reticle 2 is so configured that the resist 7 having a predetermined pattern is coated on its translucent substrate 6. The translucent substrate 6 is made of, for example, glass, quartz, or the like. The pellicle 3 is so configured that a barrier layer (protective film) 3f made of an ultra-thin metal film or the like is formed on one end portion 8f of a pellicle frame 8 in a stretched manner. The pellicle 3 is secured through another end portion 8p of the pellicle frame 8 to the reticle cassette 4 in a closely contacted state. The reticle cassette 4 is made up of two pieces of plate members (flat plates) 9 and 10 closely contacted with each other. Each of the plate members 9 and 10 is hollowed so as to have a predetermined shape. The plate member 9 after being hollowed, as shown in FIG. 1, has a shape that allows the reticle 2 to be received and housed and, in general, being square in shape. The plate member 10 after being hollowed, as shown in FIG. 1, has a shape that surrounds a circumference of the resist 7 coated on the reticle 2. As a result, a surface surrounding a hollowed portion 10h formed in the plate member 10 making up the reticle cassette 4 serves as a mounting surface 10p on which the reticle 2 to be inserted via a hollowed portion 9h of the plate member 9 is put.

Sealed space is formed in a portion surrounded by a surface of the reticle 2, on which the resist is coated, placed on the mounting surface 10p in a closely contacted state via the hollowed portion 9h of the reticle cassette 4 configured as above, by the plate member 10, pellicle frame 8, and protective film 3f. The space is so formed as to have an interval distance between the resist 7 coated on the reticle 2 and the protective film 3f being long enough to keep generated gas 20 trapped therein. The distance is set within a range between, for example, 1 mm to 6 mm.

Next, by referring to FIG. 1, functions of the reticle mounting/housing device of the first exemplary embodiment are described. To the reticle cassette 4 is secured the other end portion 8p of the pellicle frame 8 in a closed contacted state and on one end portion 8f of the pellicle frame 8 is attached the protective film 3f in a stretched manner. By inserting the reticle 2 into the hollowed portion 9h of the reticle cassette 4 by a proper mounting means, for example, a vacuum-assisted detachable means and by placing the reticle 2 on the mounting surface 10p of the reticle cassette 4 in a closed contacted state, the sealed space can be formed on the surface of the reticle 2 on which the resist is formed. Thus, simply by placing the reticle 2 on the mounting surface 10p of the reticle cassette 4, that is, only by contact between their surfaces, the sealed space can be formed. Also, the sealed space can be removed by setting the reticle 2 apart from the mounting surface 10p, which provides a great advantage in handling the reticle 2.

Accordingly, by configuring as above, the release of the gas 20 produced from the resist 7 to the outside of the photomask can be prevented when light 31 is applied via a lens 30 to the resist 7. Here, reflected light 32 is generated from the reticle 2 irradiated with the light 31. Moreover, the above configuration serves to prevent the degradation in performance of optical elements such as the lens 30 and cleaning of the lens 30 becomes unnecessary. No replacement of the lens 30 requiring high costs and long delivery time is needed, thereby saving costs and time greatly.

Thus, according to the configurations of the reticle mounting/housing device according to the first exemplary embodiment, by the separation between the reticle 2 and reticle cassette 4, a means having a great advantage can be provided and the release of the gas 20 to the outside of the photomask 1 can be prevented, which serves to maintain the performance of the optical system and to obtain effects by the avoidance of replacement of the optical system.

Second Exemplary Embodiment

Figure 2:
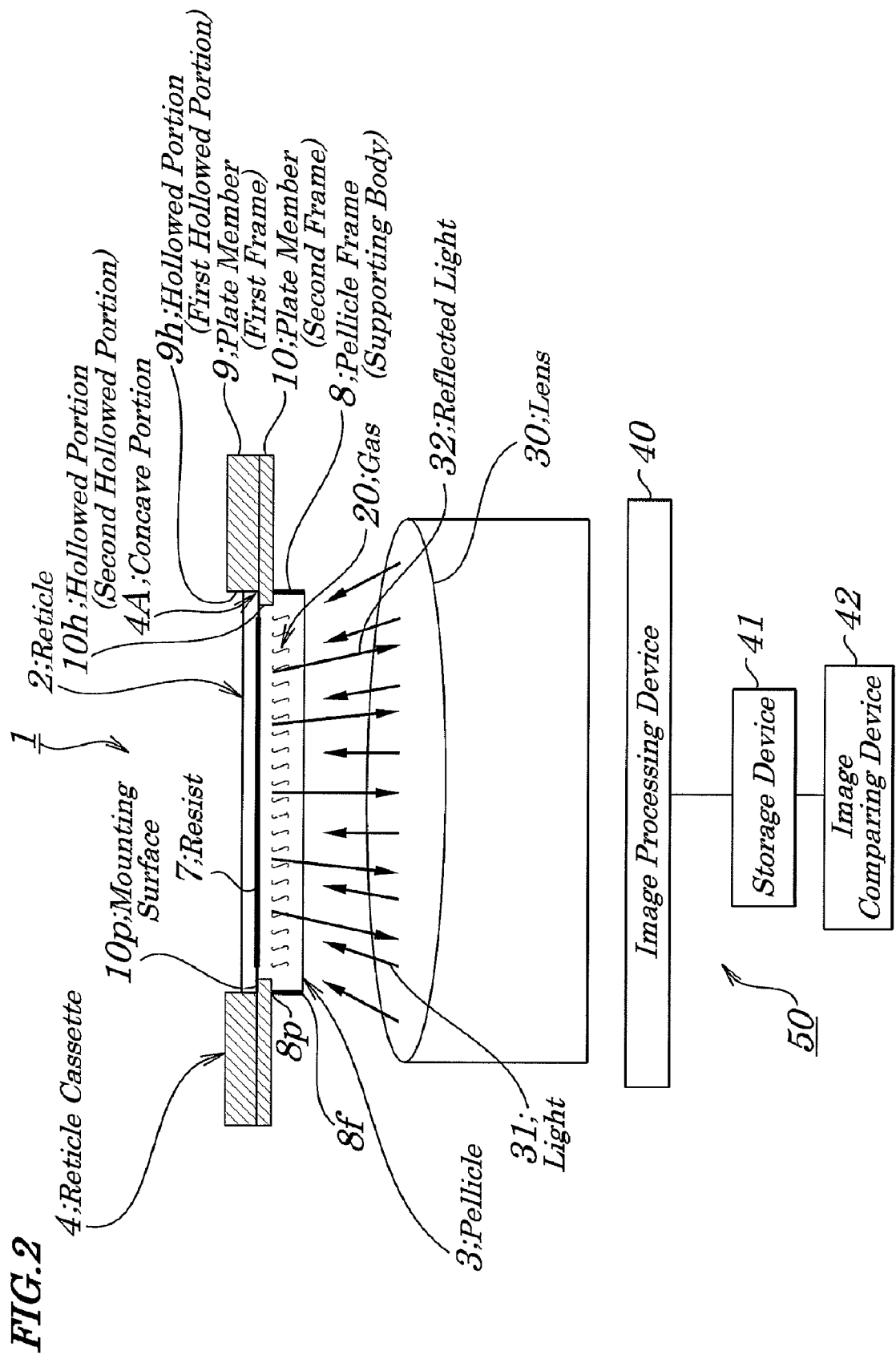
FIG. 2 is a diagram showing a resist inspection apparatus for a reticle according to a second exemplary embodiment of the present invention.
Figure 3:
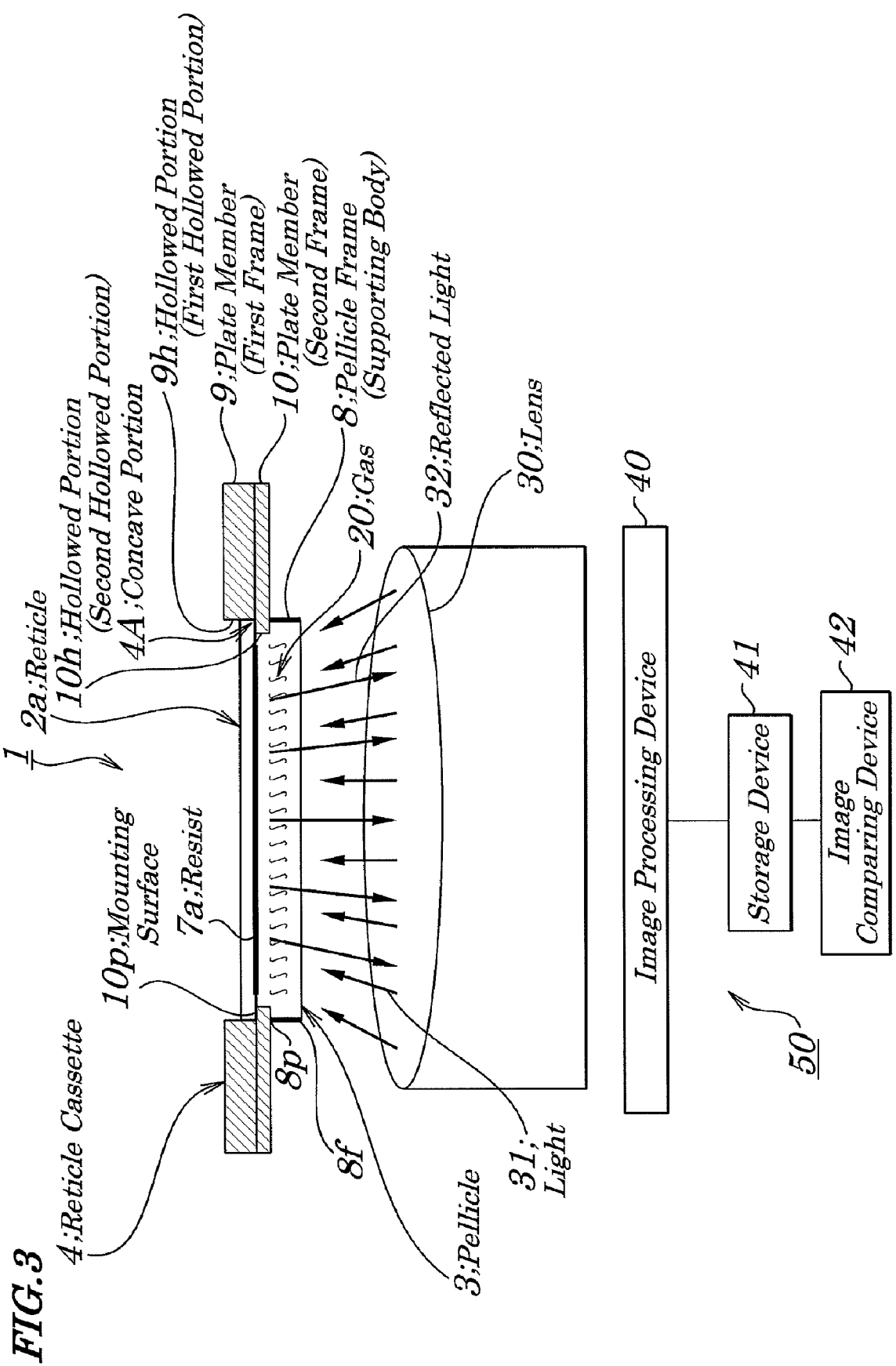
FIG. 3 is a diagram explaining a significance of the resist inspection apparatus for the reticle according to the second exemplary embodiment of the present invention.
Figure 4:
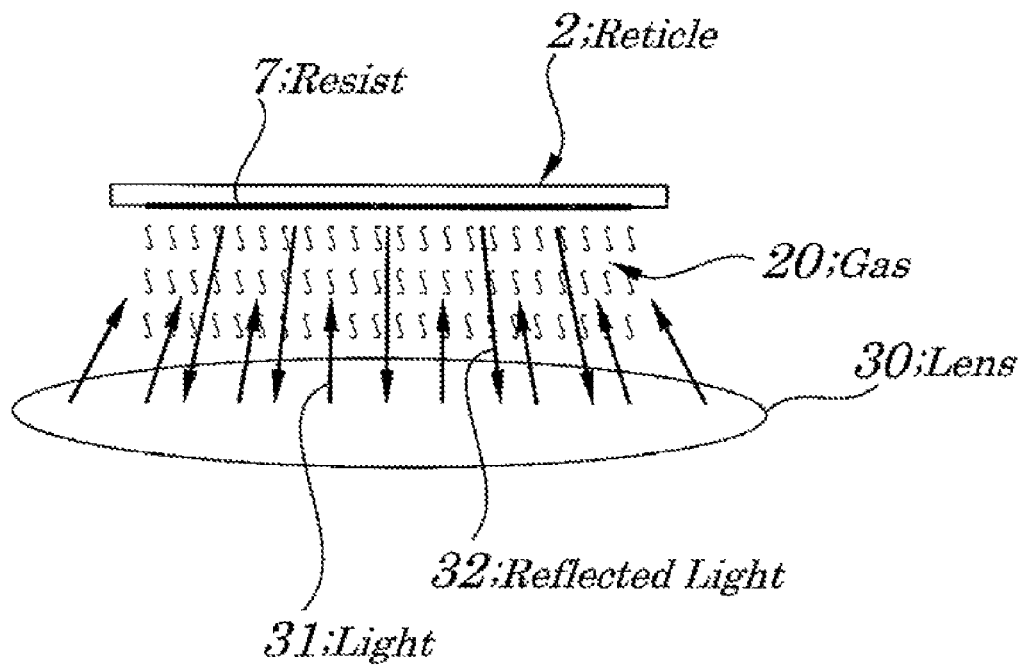
FIG. 4 is a diagram explaining a first related resist inspection apparatus.
Figure 5:
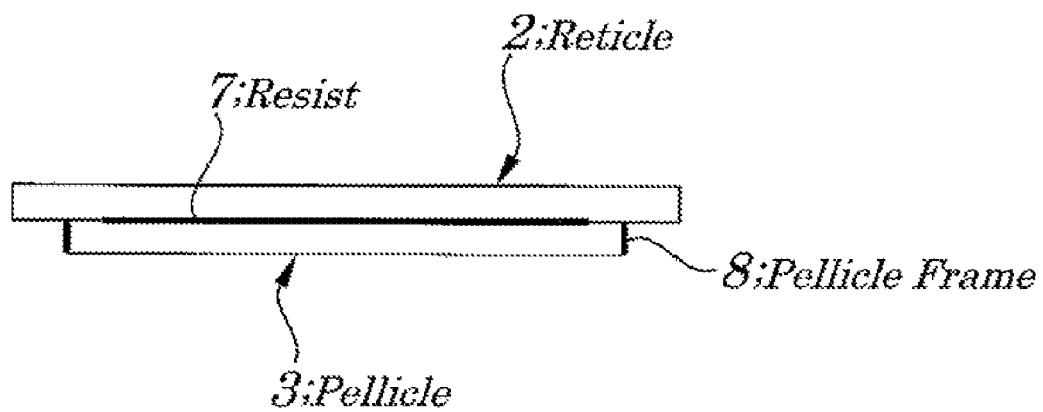
FIG. 5 is a diagram explaining configurations of a photomask used in a second related resist inspection apparatus.

FIG. 2 is a diagram showing a resist inspection apparatus for a reticle of the second exemplary embodiment of the present invention. FIG. 3 is a diagram explaining a significance of the resist inspection apparatus for a reticle of the second exemplary embodiment. The configuration of the resist inspection apparatus of the second exemplary embodiment differs from that of the first exemplary embodiment in that she reticle cassette employed in the first exemplary embodiment is used for the resist inspection apparatus for the reticle. The resist inspection apparatus 50, as shown in FIG. 2, chiefly includes a reticle cassette 4 placed in a placing portion in the resist inspection apparatus 50, a lens 30, an image processing device 40, a storage device 41, and an image comparing device 42. In the reticle cassette 4 is housed a reticle 2. The configurations other than those of the reticle cassette 4 are the same as those in the first exemplary embodiment and the same reference numbers are assigned to the same components and their detailed descriptions are omitted accordingly.

Next, by referring to FIGS. 2 and 3, operations of the resist inspection apparatus 50 of the second exemplary embodiment are described. Prior to an inspection of a resist 7 coated on the reticle 2, a reticle cassette 4 is placed on the placing portion of the resist inspection apparatus 50 in which the reticle 2 is housed in a manner in which the resist 7 on the reticle 2 is directed toward a pellicle 3. The reticle 2 is not mechanically coupled to the reticle cassette 4 and both are configured to be freely contacted with or separated from each other. Therefore, when etching is to be performed without any defect or when the reticle 2 is to be recoated with the resist 7, the process of attachment/detachment of such the pellicle 3 as employed in the Patent Reference 3 becomes unnecessary. As a result, contamination and/or damage of the reticle 2 can be prevented, whereby the number of process steps can be reduced and the process time can be shortened. Also, an easiness of a replacement of the pellicle frame 8 and/or the pellicle 3 can be achieved.

Figure 6:
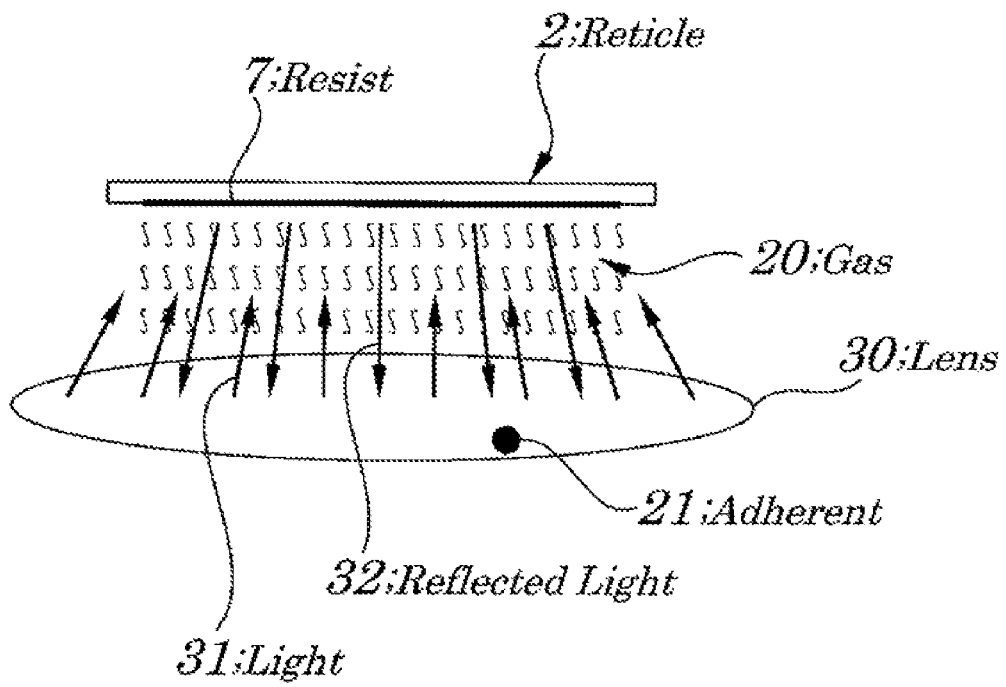
FIG. 6 is a diagram explaining one defect of the above related resist inspection apparatus.
Figure 7:
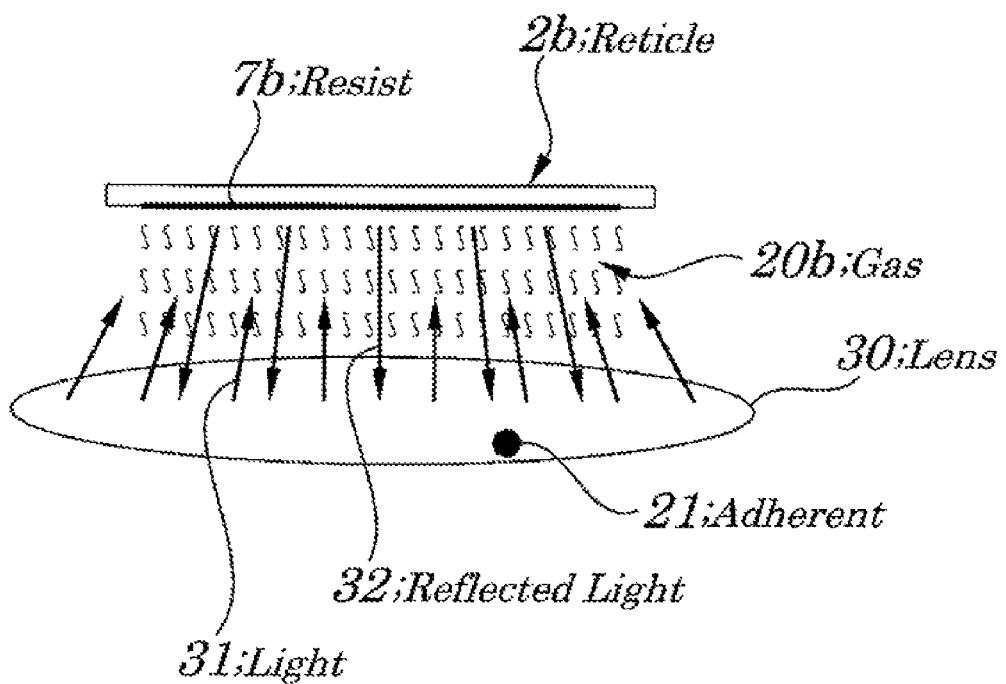
FIG. 7 is a diagram explaining another defect of the above related resist inspection apparatus.

When the inspection of the resist 7 is started by the resist inspection apparatus 50, light 31 for inspection is applied from an optical system containing a lens 30 for capturing an image to a surface having the resist 7 coated on the reticle 2 through the protective film 3f of the pellicle 3. The application of the light 31 causes gas 20 to be released from the resist 7. The released gas 20 is trapped in sealed space formed between the reticle cassette 4 and the reticle 2. Therefore, no gas 20 is left as an adherent 21 (see FIG. 6) on an optical element such as the lens 30, whereby degradation in performance of the optical element such as the lens 30 can be prevented.

The resist inspection can be performed in a state where the residual adherent 21 is prevented. When the inspection light 31 is applied to the surface of the reticle 2 on which the resist has been coated, the reflected light 32 is produced which contains a pattern image of the resist 7 and the produced pattern image is processed by the image processing device 40 and the processed pattern image is stored in the storage device 41. By inputting the pattern image stored in the storage device 41 and a predesigned pattern image using the image comparing device 42, only an actual defect of the resist 7 can be extracted.

This can be realized owing to the following reason. That is, as described above, when the inspecting light 31 is applied to the resist 7 on the reticle 2, the gas 20 is released from the resist 7, however, the released gas 20 is trapped in the sealed space formed by the reticle 2, reticle cassette 4, and pellicle 3 and is not left as the adherent 21 on the image capturing lens 30. Thus, since the gas 20 is not left as the adherent 21 on the image capturing lens 30 by configuring as above, even when the inspection of an resist of another reticle 2a set in the reticle cassette 4 (see FIG. 3) is performed by using the same resist inspection apparatus 50 used in the previous inspection, no adherent 21 produced during the previous inspection is left on the lens 30 and, further, no adherent 21 is produced during the present inspection and, as a result, no degradation in performance of the lens 30 occurs and there is no trouble in the resist inspection. That is, by using the same resist inspection apparatus 50, it is made possible to sequentially and repeatedly perform the inspection of a plurality of reticles 2. As described above, the reticle cassette 4 and reticle 2 are configured so as to be separated from each other, thereby enabling easy etching performed after being inspected and easy recoating with the resist 7.

The above sealed space is formed in the way described above and, therefore, the air purge configuration and sealed structure of electrical elements such as the lens 30 employed in the resist inspection apparatus disclosed in the Patent Reference 2 become unnecessary, whereby costs can be reduced and easiness of the maintenance can be achieved. Also, by using, as the material for the pellicle 3 forming the above sealed space, the gas barrier film such as an ultra-thin metal film, an anti-gas characteristic is enhanced. Moreover, in the case of the gas barrier film, costs for making the material ultra-thin can be reduced when compared with other materials such as, for example, glass or plastic. The term "ultra-thin" denotes the thickness of several microns. This thickness is a value to be determined from a viewpoint of a possibility that a variation in optical aberration to the light 31 for inspection occurring at a time of the replacement of the pellicle 3 gets in the way of the inspection.

Though the gas 20 adheres to the pellicle 3, since the reticle cassette 4 and/or pellicle 3 are so configured as to be easily replaced, by replacing either or both of the reticle cassette 4 and pellicle 3, the problem occurring in the Patent Reference 1 can be solved.

Thus, according to the second exemplary embodiment, the reticle 2 is not mechanically and rigidly coupled to the reticle cassette to which the pellicle is attached and the reticle 2 can be easily separated from the reticle cassette 4. The pellicle frame 8 and pellicle 3 can be easily replaced. Neither the contamination nor the damage of the reticle 2 occurs during the inspection of the reticle 2 and, further, the number of inspection process steps can be reduced and the required time for the inspection can be shortened. Moreover, since the reticle cassette 4 and reticle 2 are so configured as to be separated from each other, the etching after being inspected and recoating with the resist 7 can be easily performed. Even when resists on a plurality of reticles 2 are inspected, the employed optical elements are not affected by the gas released from the resist 7. To avoid the influence of the gas, the only thing that is needed is a means to form the sealed space between the reticle cassette 4 and reticle 2, whereby other types of means are not required.

While the invention has been particularly shown and described with reference to exemplary embodiments thereof, the invention is not limited to these exemplary embodiments. It will be understood by those of ordinary skill in the art that various changes in form and details may be made therein without departing from the spirit and scope of the present invention as defined by the claims. For example, in the above exemplary embodiments, the reticle cassette 4 is made up of two pieces of the plate members 9 and 10, however, the reticle cassette 4 may be configured by forming a concave portion in a single member to form a hollowed portion at a bottom wall in the concave portion and to cover the hollowed portion with the pellicle.

The photomask mounting/housing device and resist inspection method and resist inspection apparatus disclosed in the present invention can be applied to a field such as an EUV (Extreme UltraViolet) mask and a mask high-definition mask for FPD (Flat Panel Display) in which their masters are extremely expensive and costs for processing after a writing of patterns are high.

What is claimed is:

1. A photomask mounting/housing device for receiving and housing a photomask comprising:
a first frame body having a first hollowed portion with a shape allowing said photomask to be received and housed;
a second frame body, coupled to said first frame body, in a combined manner, and having a second hollowed portion with a shape allowing at least a resist forming region of said photomask to be inserted, such that a concave portion is formed between said first hollowed portion in said first frame body and said second hollowed portion in said second frame body; and
a translucent protective member disposed outside said second hollowing portion in said second frame body to form sealed space so as to be opposite to and be apart from said resist.

2. The photomask mounting/housing device according to claim 1, wherein said translucent protective member comprises a supporting body formed along an entire circumference of said second hollowed portion and a translucent protective film formed, in a stretched manner, along an entire circumference of a free end of said supporting body.

3. The photomask mounting/housing device according to claim 2, wherein said translucent protective film is an ultra-thin metal film.

4. The photomask mounting/housing device according to claim 2, wherein a distance between said resist and said translucent protective film is between 1 mm and 6 mm.

5. The photomask mounting/housing device according to claim 1, wherein said first frame body is a flat plate and said second frame body is also a flat plate.

6. A resist inspection method for applying light to a photomask and inspecting a resist of said photomask by receiving reflected light from said photomask, comprising:
a step of housing said resist of said photomask into a concave portion of a photomask mounting/housing device having a first frame body having a first hollowed portion with a shape allowing said photomask to be received and housed, and a second frame body, coupled to said first frame body, in a combined manner, and having a second hollowed portion allowing at least a resist forming region of said photomask to be inserted, such that a concave portion is formed between said first hollowed portion in said first frame body and said second hollowed portion in said second frame body, and a translucent protective member disposed outside said second hollowing portion in said second frame body to form sealed space so as to be opposite to and be apart from said resist, with said resist of said photomask directed toward said translucent protective member side; and
a step of applying light from said translucent protective member side to perform inspection of said resist.

7. The resist inspection method according to claim 6, wherein said translucent protective member comprises a supporting body formed along the entire circumference of said second hollowed portion and a translucent protective film formed, in a stretched manner, along the entire circumference of a free end of said supporting body.

8. The resist inspection method according to claim 7, wherein said translucent protective film is an ultra-thin metal film.

9. The resist inspection method according to claim 7, wherein a distance between said resist and said translucent protective film is between 1 mm and 6 mm.

10. The resist inspection method according to claim 6, wherein said first frame body is a flat plate and said second frame body is also a flat plate.

11. A resist inspection apparatus for applying light from an optical system to a photomask placed in a photomask placing portion and receiving reflected light from said photomask to perform inspection of a resist of said photomask, comprising:

a photomask mounting/housing device to be placed in said photomask placing portion which has a first frame body having a first hollowed portion with a shape allowing said photomask to be received and housed, a second frame body, coupled to said first frame body, in a combined manner, and having a second hollowed portion with a shape allowing at least a resist forming region of said photomask to be inserted, such that a concave portion is formed between said first hollowed portion in first frame body and said second hollowed portion in second frame body, and a translucent protective member disposed outside said second hollowing portion in said second frame body to form sealed space so as to be opposite to and be apart from said resist, and which houses, in said concave portion, said resist of said photomask, via said second hollowed portion, arranged so as to be directed toward said optical system.

12. The resist inspection apparatus according to claim 11, wherein said translucent protective member comprises a supporting body formed along the entire circumference of said second hollowed portion and a translucent protective film formed, in a stretched manner, along the entire circumference of a free end of said supporting body.

13. The resist inspection apparatus according to claim 12, wherein said translucent protective film is an ultra-thin metal film.

14. The resist inspection apparatus according to claim 12, wherein a distance between said resist and said translucent protective film is between 1 mm and 6 mm.

15. The resist inspection apparatus according to claim 11, wherein said first frame body is a flat plate and said second frame body is also a flat plate.

* * * * *